(12) United States Patent
Kibenich et al.

(10) Patent No.: US 10,392,597 B2
(45) Date of Patent: Aug. 27, 2019

(54) TEXTURIZING LACTIC ACID BACTERIA STRAINS

(71) Applicant: CHR. HANSEN A/S, Hoersholm (DK)

(72) Inventors: Annette Kibenich, Hvidovre (DK); Kim Ib Soerensen, Farum (DK); Eric Johansen, Hoersholm (DK)

(73) Assignee: Chr. Hanse A/S, Hoersholm (DK)

( * ) Notice: Subject to any disclaimer, the term of this patent is extended or adjusted under 35 U.S.C. 154(b) by 189 days.

(21) Appl. No.: 15/272,016

(22) Filed: Sep. 21, 2016

(65) Prior Publication Data

US 2017/0009198 A1    Jan. 12, 2017

Related U.S. Application Data

(62) Division of application No. 13/880,620, filed as application No. PCT/EP2011/068478 on Oct. 21, 2011, now Pat. No. 9,453,231.

(30) Foreign Application Priority Data

Oct. 22, 2010   (EP) ..................................... 10188511

(51) Int. Cl.

| | | |
|---|---|---|
| C12N 1/20 | (2006.01) | |
| A23C 9/123 | (2006.01) | |
| C12N 15/01 | (2006.01) | |
| C12R 1/225 | (2006.01) | |
| C12R 1/46 | (2006.01) | |
| C12N 15/74 | (2006.01) | |

(52) U.S. Cl.
CPC .............. *C12N 1/20* (2013.01); *A23C 9/1238* (2013.01); *C12N 15/01* (2013.01); *C12N 15/746* (2013.01); *C12R 1/225* (2013.01); *C12R 1/46* (2013.01); *A23Y 2220/15* (2013.01); *A23Y 2220/29* (2013.01); *A23Y 2240/75* (2013.01)

(58) Field of Classification Search
CPC .............. A23C 9/1238; A23Y 2220/15; A23Y 2240/75; A23Y 2220/29; C12N 1/20; C12N 15/746; C12N 15/01; C12R 1/225; C12R 1/46

See application file for complete search history.

(56) References Cited

U.S. PATENT DOCUMENTS

| | | | |
|---|---|---|---|
| 4,425,366 A | 1/1984 | Sozzi et al. | |
| 7,241,610 B2 | 7/2007 | Anba et al. | |
| 7,582,743 B2 | 9/2009 | Horvath et al. | |
| 8,865,238 B2 | 10/2014 | Janzen et al. | |
| 9,060,524 B2 | 6/2015 | Janzen et al. | |
| 9,562,221 B2 | 2/2017 | Janzen et al. | |
| 2002/0106754 A1 | 8/2002 | Tauch et al. | |
| 2004/0009490 A1 | 1/2004 | Glenn et al. | |
| 2006/0099197 A1 | 5/2006 | Farmer | |
| 2006/0240539 A1 | 10/2006 | Horvath et al. | |
| 2008/0063752 A1 | 3/2008 | Perez Martinez et al. | |
| 2008/0317903 A1 | 12/2008 | Stuer-Lauridsen et al. | |
| 2009/0061046 A1 | 3/2009 | Tams et al. | |
| 2012/0301575 A1 | 11/2012 | Janzen et al. | |
| 2013/0164408 A1 | 6/2013 | Folkenberg et al. | |
| 2013/0344199 A1 | 12/2013 | Kibenich et al. | |
| 2015/0322415 A1 | 11/2015 | Janzen et al. | |
| 2017/0298457 A1 | 10/2017 | Janzen et al. | |

FOREIGN PATENT DOCUMENTS

| | | |
|---|---|---|
| CN | 101175848 A | 5/2008 |
| CN | 101384701 A | 3/2009 |
| CN | 101505607 A | 8/2009 |
| CN | 103025863 B | 11/2015 |
| JP | H05-168467 | 7/1993 |
| JP | H10-215861 A | 8/1998 |
| JP | H11-103854 A | 4/1999 |
| JP | 2003-158997 A | 6/2003 |
| JP | 2005-519597 | 7/2005 |
| JP | 2006-501843 | 1/2006 |
| JP | 2006-520590 | 9/2006 |
| JP | 2009-527233 | 7/2009 |
| JP | 2013-503604 A | 2/2013 |
| JP | 2013-517785 A | 5/2013 |
| JP | 2013-529461 A | 7/2013 |
| RU | 2141521 C1 | 11/1999 |
| WO | WO-03/096816 | 11/2003 |
| WO | WO-2004/085607 A2 | 10/2004 |
| WO | WO-2004/089098 A1 | 10/2004 |
| WO | WO-2006/072631 | 7/2006 |
| WO | WO-2007/025097 A2 | 3/2007 |
| WO | WO-2007/095958 A1 | 8/2007 |
| WO | WO-2007/144770 A2 | 12/2007 |

(Continued)

OTHER PUBLICATIONS

Non-Final Office Action issued in co-pending U.S. Appl. No. 15/360,298, dated May 30, 2018 (US 2017/0298457).
Santos, et al., "Combination Engineering of Microbes for Optimizing Cellular Phenotype," Curr. Opin. Chem. Biol., vol. 12, pp. 168-176 (Feb. 2008).
Sturino, et al., "Bacteriophage Defense Systems and Strategies," Advances in Applied Microbiology, vol. 56, pp. 332-338 (2004).
Dictionary Definition of the Term "Genetic Engineering," obtained from oxforddictionaries.com, 1 page, last viewed May 23, 2018.

(Continued)

*Primary Examiner* — Satyendra K Singh

(74) *Attorney, Agent, or Firm* — Foley & Lardner LLP

(57) ABSTRACT

The present invention relates to mutants of lactic acid bacteria which are resistant towards the antibiotic D-cycloserine and/or functionally equivalent antibiotics and which were found to give an increased texture when grown in milk while maintaining the other growth properties of the parent strain. The present invention, furthermore, relates to compositions comprising such mutants, and to dairy products fermented with the lactic acid bacteria resistant towards D-cycloserine and/or functionally equivalent antibiotics.

13 Claims, 3 Drawing Sheets

(56) References Cited

FOREIGN PATENT DOCUMENTS

| WO | WO-2007/147890 A1 | 12/2007 |
| WO | WO-2008/040734 A1 | 4/2008 |
| WO | WO-2008/092458 A1 | 8/2008 |
| WO | WO-2008/148561 A1 | 12/2008 |
| WO | WO-2010/023178 A1 | 3/2010 |
| WO | WO-2011/000879 A2 | 1/2011 |
| WO | WO-2011/000883 A2 | 1/2011 |
| WO | WO-2011/092300 A1 | 8/2011 |

OTHER PUBLICATIONS

Akcelik, Mustafa, et al., "Characterisation of an Exopolysaccharide Preventing Phage Adsorption in *Lactococcus lactic* subsp. cremoris MA39", Turkish Journal of Veterinary and Animal Sciences, 26(5): 1151-1156 (2002).

Akpinar, Asli, et al.; "Antimicrobial activity and antibiotic resistance of *Lactobacillus delbrueckii* ssp. *bulgaricus* and *Streptococcus thermophilus* strains isolated from Turkish homemade yoghurts"; African Journal of Microbiology Research, 5(6): 675-682 (Mar. 2011).

Andre, et al., "Imaging the nanoscale organization of peptidoglycan in living Lactococcus lactis cells", Nature Communications, 1(27): 1-8 (Jun. 2010).

Bhaskaracharya, et al., "Texture characteristics and microstructure of skim milk mozzarella cheeses made using exopolysaccharide or non-exopolysaccharide producing starter cultures", The Australian Journal of Diary Technology, 55(3): 132-138 (Oct. 2000).

Bonisch, et al., "Transglutaminase cross-linking of milk proteins and impact on yoghurt gel properties," International Dairy Journal, 17(11): 1360-1371 (Nov. 2007).

Bouzar, F., et al.; "Exopolysaccharide Production and Texture-Promoting Abilities of Mixed-Strain Starter Cultures in Yogurt Production"; Journal of Dairy Science, 80(10): 2310-2317 (Oct. 1997).

Broadbent, J.R. et al., "Biochemistry, Genetics, and Applications of Exopolysaccharide Production in *Streptococcus thermophilus*: a Review", Journal of Dairy Science, 86(2): 407-423 (Feb. 2003).

Bron et al., "Use of the alr Gene as a Food-Grade Selection Marker in Lactic Acid Bacteria," Applied and Environmental Microbiology, 68(11):5663-5670 (Nov. 2002).

Caceres et al., "Overexpression of the D-Alanine Racemase Gene Confers Resistance to D-Cycloserine in *Mycobacterium smegmatis*," Journal of Bacteriology, 179(16):5046-5055 (Aug. 1997).

D'Aimmo et al.; "Antibiotic resistance of lactic acid bacteria and *Bifidobacterium* spp. isolated from dairy and pharmaceutical products"; International Journal of Food Microbiology, 115:35-42 (Apr. 2007).

De Vin, Filip, et al., "Molecular and Biochemical Analysis of the Galactose Phenotype of Dairy *Streptococcus thermophilus* Strains Reveals Four Different Fermentation Profiles", Applied and Environmental Microbiology, 71(7): 3659-3667 (Jul. 2005).

De Vuyst, L., et al.; "Heteropolysaccharides from lactic acid bacteria"; FEMS Microbiology Reviews 23: 153-177 (Apr. 1999).

Delcour et al., "The Biosynthesis and Functionality of the Cell-Wall of Lactic Acid Bacteria," Antonie van Leeuwenhoek, 76:159-184, (1999).

Derkx, et al.; "The art of strain improvement of industrial lactic acid bacteria without the use of recombinant DNA technology": Microbial Cell Factories, 13(Suppl 1:S5):1-13 (Aug. 2014).

European Search Report issued in Application No. 10166614.7 dated Nov. 4, 2010.

Forde, A., et al., "Bacteriophage defence systems in lactic acid bacteria", Antonie van Leeuwenhoek, 76(1-4): 89-113 (1999).

Goffin et al., "Lactate Racemization as a Rescue Pathway for Supplying D-Lactate to the Cell Wall Biosynthesis Machinery in Lactobacillus plantarum," Journal of Bacteriology, 187(19): 6750-6761 (Oct. 2005).

Guglielmotti, Daniela M.,et al., "Probiotic potential of Lactobacillus delbrueckii strains and their phage resistant mutants," International Diary Journal, 17: 916-925 (Aug. 2007).

Handa, et al., "Rapid and Reliable Site-Directed Mutagenesis Using Kunkel's Approach," Methods in Molecular Biology, 182: 1-6 (J. Braman ed., $2^{nd}$ ed., Feb. 2002).

Hassan, A. N. et al. "Microstructure and rheology of yogurt made with cultures differing only in their ability to produce exopolysaccharides", Journal of Dairy Science, 86(5): 1632-1638 (May 2003).

Hess, S. J. et al. "Rheological Properties of Nonfat Yogurt Stabilized Using *Lactobacillus delbrueckii* ssp. *bulgaricus* Producing Exopolysaccharide or Using Commercial Stabilizer Systems", Journal of Dairy Science; 80(2): 252-263 (Feb. 1997).

Hols et al., "Conversion of Lactococcus lactis from homolactic to homoalanine fermentation through metabolic engineering," Nature Biotechnology 17(6): 588-592 (Jun. 1999).

Holtje, "Cell Walls, Bacterial," in The Desk Encyclopedia of Microbiology, chapter 19:239-250 (M. Schaechter ed., Dec. 2003).

Nauth, "Yogurt" in Handbook of Food and Beverage Fermentation Technology, Chapter 7; (Hui et al. eds., 2004).

Hutkins, et al., "Use of Galactose-Fermenting *Streptococcus thermophiles* in the Manufacture of Swiss, Mozzarella, and Short-Method Cheddar Cheese," Journal of Dairy Science, 69(1): 1-8 (May 1986).

Levander, Fredrik, et al., "Enhanced Exopolysaccharide Production by Metabolic Engineering of *Streptococcus thermophilus*", Applied and Environmental Microbiology, 68(2): 784-790 (Feb. 2002).

Li, et al., "Non-antibiotic Resistance Selection Marker Systems for Lactic Acid Bacteria," Chinese Journal of Biochemistry and Molecular Biology, 23 (1): 1-7 (2007).

Marshall, et al., "Structural characterization of the exopolysaccharide produced by *Streptococcus thermophilus* EU20," Carbohyrdate Research, 332: 413-422 (Apr. 2001).

Mozzi, F., et al., "Effect of galactose and glucose on the exopolysaccharide production and the activities of biosynthetic enzymes in Lactobacillus casei CRL 87", Journal of Applied Microbiology, 91, 160-167 (Jul. 2001).

Park et al., "D-Alanyl-D-Lactate and D-Alanyl-D-Alanine Synthesis by D-Alanyl-D-Alanine Ligase from Vancomycin-resistant Leuconostoc mesenteroides: Effects of a phenylalanine 261 to tyrosine mutation," The Journal of Biological Chemistry, 272(14):9210-9214 (Apr. 1997).

PCT International Search Report issued in Application No. PCT/EP2010/062808 dated Oct. 12, 2010.

PCT International Search Report issued in Application No. PCT/EP2011/051239 dated Mar. 24, 2011.

PCT International Search Report issued in Application No. PCT/EP2011/060302 dated Sep. 30, 2011.

PCT International Search Report issued in Application No. PCT/EP2011/068478, dated Nov. 22, 2011.

PCT Written Opinion issued in Application No. PCT/EP2011/068478 dated Feb. 20, 2013.

Rivals et al., "Cryotolerance of *Lactobacillus delbrueckii* Subsp. *bulgaricus* CFL1 is modified by acquisition of antibiotic resistance," Cryobiology, 55:19-26 (Apr. 2007).

Robitaille, G., et al., "Fat-free yogurt made using a galactose-positive exopolysaccharide-producing recombinant strain of *Streptococcus thermophilus*", J. Dairy Science, 92(2): 477-482 (Feb. 2009).

Robitaille, G., et al., "Galactose Metabolism and Capsule Formation in a Recombinant Strain of *Streptococcus thermophilus* with a Galactose-Fermenting Phenotype", Journal of Dairy Science, 90(9): 4051-4057 (Sep. 2007).

Lucchini, Sacha., et al., "Broad-Range Bacteriophage Resistance in *Streptococcus thermophilus* by insertional Mutagenesis", Virology; 275: 267-277 (Sep. 2000).

Sudi, Ismaila Y., et al.; "Mutagenesis and Selection of Lactobacillus bulgaricus and *Streptococcus thermophilus* for Potential use as Starter Culture"; The Journal of American Science, 4(3): 80-87 (2008).

(56) References Cited

OTHER PUBLICATIONS

Svensson, M., et al., "Altered nucleotide sugar metabolism in *Streptococcus thermophilus* interferes with nitrogen metabolism", International Journal of Food Microbiology, 113(2): 195-200 (Jan. 2007).

Tang, Huan, et al.; "Antibiotic susceptibility of strains in Chinese medical probiotic products"; Journal of Medical Colleges of PLA, 22(3): 149-152 (Jun. 2007).

Tytgat et al., "DD-Ligases as a Potential Target for Antibiotics: Past, Present and Future," Current Medicinal Chemistry, 16:2566-2580 (Jul. 2009).

USPTO Final Office Action issued in U.S. Appl. No. 13/393,343 (US 2012-0164275) dated Feb. 26, 2015.

USPTO Final Office Action issued in U.S. Appl. No. 13/393,343 (US 2012-0164275) dated Sep. 19, 2013.

USPTO Final Office Action issued in U.S. Appl. No. 13/880,620 (US 2013-0344199) dated Nov. 12, 2015; 17 pages.

USPTO Final Office Action issued in U.S. Appl. No. 13/805,988 (US 2013-0164408) dated Mar. 24, 2015.

USPTO Final Office Action issued in U.S. Appl. No. 13/805,988 (US 2013-0164408) dated Aug. 10, 2016.

USPTO Non-final Office Action issued in U.S. Appl. No. 15/045,932 (US 2016-0227803) dated May 18, 2016; 7 pages.

USPTO Non-final Office Action issued in U.S. Appl. No. 13/393,343 (US 2012-0164275) dated May 14, 2013.

USPTO Non-final Office Action issued in U.S. Appl. No. 13/393,343 (US 2012-0164275) dated Oct. 26, 2015.

USPTO Non-final Office Action issued in U.S. Appl. No. 13/393,343 (US 2012-0164275) dated Sep. 24, 2014.

USPTO Non-final Office Action issued in U.S. Appl. No. 13/575,922 (US 2012-0301575) dated Nov. 20, 2013.

USPTO Non-final Office Action issued in U.S. Appl. No. 13/805,988 (US 2013-0164408) dated Sep. 26, 2014.

USPTO Non-final Office Action issued in U.S. Appl. No. 13/805,988 (US 2013-0164408)dated Mar. 25, 2016.

USPTO Non-final Office Action issued in U.S. Appl. No. 13/880,620 (US 2013-0344199) dated May 1, 5025.

USPTO Non-final Office Action issued in U.S. Appl. No. 14/719,058 (US 2015-0322415) dated Nov. 20, 2015.

USPTO Notice of Allowance issued in U.S. Appl. No. 13/575,922 (US 2012-0301575) dated Jun. 18, 2014.

USPTO Notice of Allowance issued in U.S. Appl. No. 13/880,620 (US 2013-0344199) dated May 24, 2016; 19 pages.

USPTO Notice of Allowance issued in U.S. Appl. No. 14/500,134 (US 2015-0099273) dated Feb. 18, 2015.

USPTO Notice of Allowance issued in U.S. Appl. No. 14/719,058 (US 2015-0322415) dated Apr. 12, 2016; 8 pages.

USPTO Office Action issued in U.S. Appl. No. 13/880,620 (US 2013-0344199) dated Oct. 1, 2014.

Vaillancourt, Katy, et al., "Characterization of a Galactokinase-Positive Recombination Strain of *Streptococcus thermophilus*", Applied and Environmental Microbiology, 70(8):4596-4603(Aug. 2004).

Vedamuthu, Ebenezer R. et al., "Involvement of a Plasmid in Production of Ropiness (Mucoidness) in Milk Cultures by *Streptococcus cremoris* MS", Applied and Environmental Microbiology, 51(4): 677-682(Apr. 1986).

Vinderola, Gabriel, et al., "Phage-resistant mutants of Lactobacillus delbrueckii may have functional properties that differ from those of parent strains", International Journal of Food Microbiology, 116(1): 96-102 (May 2007) (published online Jan. 2007).

TEXTURIZING LACTIC ACID BACTERIA STRAINS

CROSS-REFERENCE TO RELATED PATENT APPLICATIONS

This application is a divisional application of U.S. patent application Ser. No. 13/880,620, filed Apr. 19, 2013, which is the U.S. National Stage of International Application No. PCT/EP2011/068478 filed Oct. 21, 2011, which was published on Apr. 26, 2012, as WO 2012/052557, which claims the benefit of EP Application No. 10188511.9, filed Oct. 22, 2010. The respective contents of these applications are incorporated here by reference in their entirety.

FIELD OF INVENTION

The present invention relates to mutants of lactic acid bacteria, such as *Lactobacillus delbrueckii* subsp *bulgaricus* and *Streptococcus thermophilus*, which are resistant towards the antibiotic D-cycloserine and/or functionally equivalent antibiotics, and which were found to give an increased texture when grown in milk while maintaining the other growth properties of the parent strain. The present invention, furthermore, relates to cultures, such as starter cultures, comprising such mutants, and to dairy products fermented with the cultures.

BACKGROUND OF INVENTION

The food industry uses numerous bacteria, in particular lactic acid bacteria, in order to improve the taste and the texture of foods but also in order to extend the shelf life of these foods. In the case of the dairy industry, lactic acid bacteria are used intensively in order to bring about the acidification of milk (by fermentation) but also in order to texturize the product into which they are incorporated.

Among the lactic acid bacteria used in the food industry, there can be mentioned the genera *Streptococcus, Lactococcus, Lactobacillus, Leuconostoc, Pediococcus* and *Bifidobacterium*. The lactic acid bacteria of the species *Streptococcus thermophilus* are used extensively alone or in combination with other bacteria such as *Lactobacillus delbrueckii* subsp *bulgaricus* for the production of food products, in particular fermented products. They are used in particular in the formulation of the ferments used for the production of fermented milks, for example yoghurts. Certain of them play a dominant role in the development of the texture of the fermented product. This characteristic is closely linked to the production of polysaccharides.

The current trend in yoghurts is for mild flavor and high texture. Today this is achieved by the use of cultures which produce a mild flavor and the addition of thickeners or protein to give the desired thickness. Yoghurt producers would like to be able to make yoghurt with these properties without the addition of thickening agents. This will help them reduce cost and give a cleaner label. One very attractive way to achieve this would be to have a starter culture which produces a high level of texture.

In order to meet the requirements of the industry, it has become necessary to provide novel texturizing strains of lactic acid bacteria, in particular of *Lactobacillus delbrueckii* subsp *bulgaricus* and *Streptococcus thermophilus*, for texturizing food products. Especially there is a need for novel texturizing strains of *Lactobacillus delbrueckii* subsp *bulgaricus* which can be used together with novel texturizing strains of *Streptococcus thermophilus*.

Mutants resistant towards D-cycloserine have been described for a number of different bacteria but it has never been reported that these mutants can be used for increasing the texture of a dairy product. Neither *Streptococcus thermophilus* nor *Lactobacillus delbrueckii* subsp *bulgaricus* mutants have been described.

SUMMARY OF THE INVENTION

The inventors of the present invention have surprisingly found that a group of lactic acid bacteria mutants resistant towards D-cycloserine generates higher shear stress and/or gel stiffness than the mother strain when the bacteria are used for fermenting milk.

The present inventors have provided a method for obtaining such texturizing lactic acid bacteria strains which are resistant towards the antibiotic D-cycloserine and/or functionally equivalent antibiotics and they have provided a novel group of D-cycloserine resistant lactic acid bacteria strains of the species *Lactobacillus delbrueckii* subsp. *bulgaricus* and *Streptococcus thermophilus* with high texturizing properties.

In accordance with the above surprising findings, the present invention relates to texturizing lactic acid bacteria strains, such as *Lactobacillus delbrueckii* subsp *bulgaricus* and *Streptococcus thermophilus* strains, which are D-cycloserine resistant and/or resistant to a functionally equivalent antibiotic and a method for obtaining such strains. Furthermore, the present invention relates to cultures, such as starter cultures, comprising the mutants and to dairy products, such as fermented milk products fermented with the cultures.

DETAILED DISCLOSURE

Definitions

Figure 1:
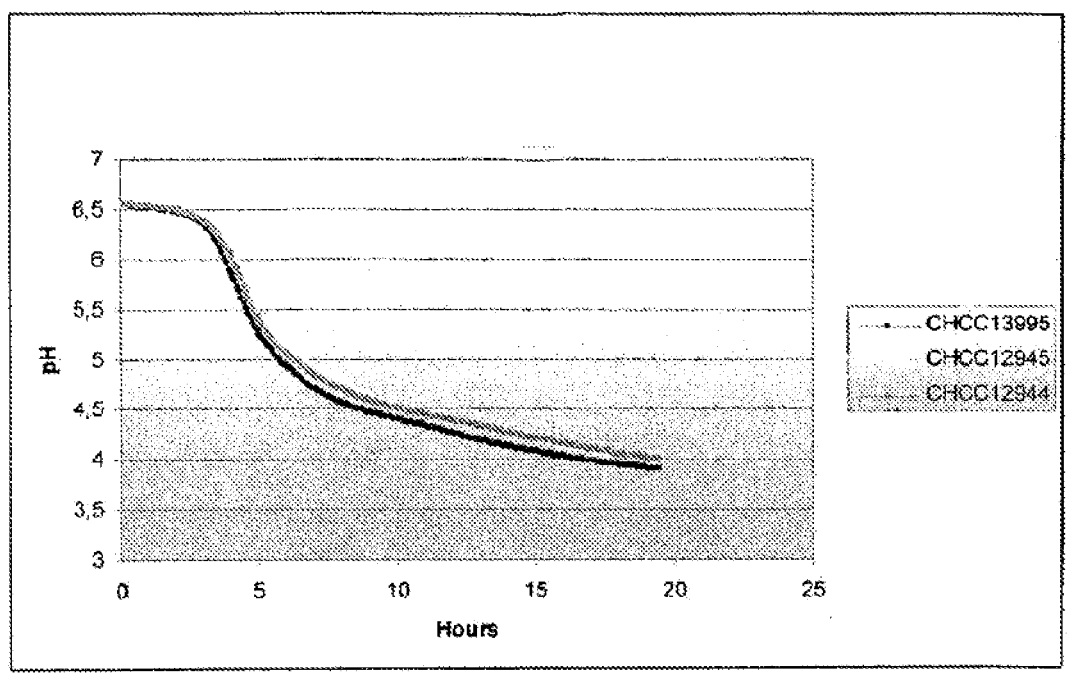
FIG. 1 shows acidification profiles (pH as a function of time) in milk at 43° C. for mother strain *Lactobacillus delbrueckii* subsp. *bulgaricus* CHCC13995 and two D-cycloserine mutants of CHCC13995 named CHCC12944 and CHCC12945.

As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pediococcus* spp., *Brevibacterium* spp., *Enterococcus* spp. and *Propionibacterium* spp. Additionally, lactic acid producing bacteria belonging to the group of the strict anaerobic bacteria, bifidobacteria, i.e. *Bifidobacterium* spp., are generally included in the group of lactic acid bacteria. These are frequently used as food cultures alone or in combination with other lactic acid bacteria. Lactic acid bacteria, including bacteria of the species *Lactobacillus* sp. and *Streptococcus thermophilus*, are normally supplied to the dairy industry either as frozen or freeze-dried cultures for bulk starter propagation or as so-called "Direct Vat Set" (DVS) cultures, intended for direct inoculation into a fermentation vessel or vat for the production of a dairy product, such as a fermented milk product. Such cultures are in general referred to as "starter cultures" or "starters".

The term "milk" is to be understood as the lacteal secretion obtained by milking any mammal, such as cows, sheep, goats, buffaloes or camels. In a preferred embodiment, the milk is cow's milk. The term milk also includes protein/fat solutions made of plant materials, e.g. soy milk.

The term "milk substrate" may be any raw and/or processed milk maternal that can be subjected to fermentation according to the method of the invention. Thus, useful milk substrates include, but are not limited to, solutions/suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any mammal, e.g. being substantially pure mammalian milk, or reconstituted milk powder.

Preferably, at least part of the protein in the milk substrate is proteins naturally occurring in milk, such as casein or whey protein. However, part of the protein may be proteins which are not naturally occurring in milk.

Prior to fermentation, the milk substrate may be homogenized and pasteurized according to methods known in the art.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

"Fermentation" in the methods of the present invention means the conversion of carbohydrates into alcohols or acids through the action of a microorganism. Preferably, fermentation in the methods of the invention comprises conversion of lactose to lactic acid.

Fermentation processes to be used in production of fermented milk products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a dairy product in solid or liquid form (fermented milk product).

In the present context, a yoghurt starter culture is a bacterial culture which comprises at least one *Lactobacillus delbrueckii* subsp *bulgaricus* strain and at least one *Streptococcus thermophilus* strain. In accordance herewith, a "yoghurt" refers to a fermented milk product obtainable by inoculating and fermenting milk with a composition comprising a *Lactobacillus delbrueckii* subsp *bulgaricus* strain and a *Streptococcus thermophilus* strain.

In the present context, the term "shear stress" determines viscosity. Viscosity (unit is Pa s) is defined as Shear Stress (Pa)/Shear rate (1/s).

Shear stress value is reported as a standard herein at shear rate=300 1/s. Sensory experiments have shown (data not shown) that the best correlation between rheological measurements and sensory viscosity/mouth thickness are found when using the viscosity measured at shear rate 300 1/s.

In the present context, the term "functionally equivalent antibiotic" should be understood as an antibiotic with the same mode of action or the same target as D-cycloserine, such as e.g. other inhibitors of D-alanyl-D-alanine ligases, such as e.g. vancomycin (Tytgat et al. (2009), Curr. Med. Chem. 16(20): 2566.2580) and other inhibitors of D-alanine racemase, such as e.g. O-carbamoyl-D-serine, alaphosphin and the haloalanines (Holtje (2004), *The Desk Encyclopedia of Microbiology*: 239-258).

The term "resistant towards D-cycloserine and/or a functionally equivalent antibiotic" herein means that a particular mutated bacterial strain is not killed, or killed significantly more slowly compared to the corresponding non-mutated strain from which the mutated strain is derived in the presence of said antibiotic in the culture medium. Dependent on the concentration of the antibiotic compound in the culture medium, resistance can also be reflected by altered growth properties of the mutated and non-mutated strains. For example, a low concentration of the antibiotic in the culture medium will prevent or significantly decrease the growth of non-mutated strains while the growth of the mutated strains is not affected. Non-mutated strains which can be used as sensitive reference strains in the assessment of resistance preferably include the strains CHCC13995 and CHCC13994.

Examples 1 and 2 of the present application exemplify the isolation of mutant strains of *Lactobacillus delbrueckii* subsp. *bulgaricus* and *Streptococcus thermophilus*, respectively, which are resistant to D-cycloserine. Based on the methods referred to in Example 1 and 2, the skilled person will be readily able to choose for each non-mutated mother strain an amount of D-cycloserine or an amount of a functionally equivalent antibiotic which is effective in killing the majority of the cells of the mother strain while not killing or killing significantly more slowly mutant strains resistant towards D-cycloserine and/or a functionally equivalent antibiotic.

In the present context, the term "mutant" should be understood as a strain derived, or a strain which can be derived from a strain of the invention (or the mother strain) by means of e.g. genetic engineering, radiation and/or chemical treatment. The mutant can also be a spontaneously occurring mutant. It is preferred that the mutant is a functionally equivalent mutant, e.g. a mutant that has substantially the same, or Improved, properties (e.g. regarding viscosity, gel stiffness, mouth coating, flavor, post acidification, acidification speed, and/or phage robustness) as the mother strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light, or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant less than 1%, less than 0.1, less than 0.01, less than 0.001% or even less than 0.0001% of the nucleotides in the bacterial genome have been replaced with another nucleotide, or deleted, compared to the mother strain.

In the present context, the term "variant" should be understood as a strain which is functionally equivalent to a strain of the invention, e.g. having substantially the same, or improved, properties e.g. regarding viscosity, gel stiffness, mouth coating, flavor, post acidification, acidification speed, and/or phage robustness). Such variants, which may be identified using appropriate screening techniques, are a part of the present invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Implementation and Aspects of the Invention

D-cycloserine (D-4-amino-isoxazolidone) is an antibiotic which inhibits alanine racemase, D-alanyl-D-alanine ligase, D-alanylalanine synthase and D-alanine permease causing cell lysis. D-alanine racemase is essential for the production of D-alanine, an integral part of the peptidoglycan layer of the cell wall. Mutants of *Mycobacterium* which are resistant to D-Cycloserine overproduce D-alanine by increasing the expression of the D-alanine racemase gene (Caceres et al. (1997), J. Bacteriol. 179: 5046-5055). Thus, the inventors of the present invention contemplated that it would be possible to isolate spontaneous mutants of lactic acid bacteria strains which naturally have a higher production of D-alanine. Such mutants were isolated and characterized.

A person of skill in the art will recognize that other antibiotics with the same mode of action or the same target as D-cycloserine can be used alone or in combination with D-cycloserine to isolate mutants of the type described here. The present invention, therefore, also encompasses the use of such other functionally equivalent antibiotics, such as other inhibitors of D-alanyl-D-alanine ligases or O-alanine racemase.

The term "functionally equivalent antibiotics to D-cycloserine" as used herein includes any compound which interferes with the synthesis of D-alanine, with the transport of D-alanine into the cell, with the formation of D-alanyl-Dalanine from D-alanine or with the inclusion of D-alanyl-D-alanine into building blocks of the peptidoglycan polymer. Such antibiotics include, but are not limited to, antibiotics that inhibit the enzymes D-alanine-racemase, D-alanyl-D-alanine ligase, D-alanylalaninse synthase and D-alanine permease. Such functionally equivalent antibiotics to D-cycloserine include, but are not limited to, vancomycin, O-carbamoyl-D-serine, alaphosphin and the haloalanines.

Some mutants of *Lactobacillus delbrueckii* subsp *bulgaricus* and *Streptococcus thermophilus* which are resistant to D-cycloserine were found to give an increased texture when grown in milk compared to the parent strain while maintaining the other growth properties of the parent strain.

In accordance with the above surprising findings, the present invention in a first aspect relates to a method for obtaining a texturizing lactic acid bacteria strain said method comprising:
 a) providing a lactic acid bacteria mother strain;
 b) isolating a mutant of the mother strain which is resistant towards D-cycloserine and/or a functionally equivalent antibiotic to D-cycloserine; and
 c) selecting the mutant if it produces more texture, as determined by greater shear stress and/or greater gel stiffness, when grown in milk than the mother strain, thereby obtaining a texturising lactic acid bacteria strain.

Thus, the first aspect relates to a method for obtaining a lactic acid bacteria mutant which results in increased shear stress and or/gel stiffness when grown in milk, said method comprising:
 a) providing a lactic acid bacteria mother strain;
 b) isolating a mutant of the mother strain which is resistant towards D-cycloserine and/or a functionally equivalent antibiotic to D-cycloserine; and
 c) selecting the mutant if it produces more texture, as determined by greater shear stress and/or greater gel stiffness, when grown in milk than the mother strain, thereby obtaining a lactic acid bacteria mutant which results in increased shear stress and/or gel stiffness when grown in milk.

The production by a selected mutant of more texture than the mother strains, as determined by greater shear stress and/or greater gel stiffness, occurs both in full fat and low-fat milk.

In a preferred embodiment the milk is cow milk. Preferably, the milk is full-fat cow milk.

In a preferred embodiment the lactic acid bacteria mother strain is a lactic acid bacteria selected from the group consisting of *Lactobacillus delbrueckii* subsp *bulgaricus* and *Streptococcus thermophilus*. However, use of other lactic acid bacteria, such as bacteria of *Lactococcus* spp., *Streptococcus* spp., *Lactobacillus* spp., *Leuconostoc* spp., *Pediococcus* spp., *Brevibacterium* spp., *Enterococcus* spp., *Propionibacterium* spp., and *Bifidobacterium* spp., are also part of the present invention.

In one preferred embodiment, mutants are obtained by incubating the lactic acid bacteria mother strain in/on growth medium containing D-cycloserine and/or a functionally equivalent antibiotic to D-cycloserine and isolating a mutant of the mother strain which is either not killed by the D-cycloserine and/or the functionally equivalent antibiotic to D-cycloserine or which is killed significantly more slowly than the majority of the non-mutated cells tested. However, the present invention encompasses other ways known to the skilled person of isolating mutants resistant to D-Cycloserine and/or functionally equivalent antibiotics to D-cycloserine. Accordingly, the mother strain used in the method of the first aspect of the present invention is a strain that is not resistant (or less resistant) to D-Cycloserine and/or the functionally equivalent antibiotic to D-cycloserine.

In one embodiment the mutant may be a spontaneous mutant resistant to D-cycloserine and/or a functionally equivalent antibiotic to D-cycloserine.

In another embodiment the method of the invention may comprise a step of mutagenising (e.g. by chemical treatment or radiation treatment, or by means of genetic engineering techniques) the mother strain, e.g. before or during step b.

Thus, in one embodiment the mutant may be obtained by mutagenesis of the mother strain by means of e.g. chemical treatment or radiation treatment, or a mutant obtained by means of genetic engineering techniques.

By "texture" or "mouthfeel" are meant the product's physical and chemical interaction in the mouth.

Methods for determining the texture of milk include measuring the shear stress (viscosity) or gel stiffness of the fermented milk and are readily available and known in the art and exemplified herein.

The mutant is selected, in step c), if it produces more texture, as determined by greater shear stress and/or greater gel stiffness, in fermented milk than the mother strain when inoculated in the same amount as the mother strain, such as in an amount of at least $10^4$ cells per mi.

In a preferred embodiment, the mutant generates a viscosity in milk measured as shear stress in 300 l/s (Pa) which is at least about 5% higher, at least about 10% higher, at least about 15% higher, at least about 20% higher, at least about 25% higher, at least about 30% higher, at least about 35% higher, at least about 40% higher, at least about 50% higher, than the viscosity generated by the mother strain.

In another embodiment, the mutant generates a gel stiffness in milk which is at least about 5% higher, at least about 10% higher, at least about 15% higher, at least about 20% higher, at least about 25% higher, at least about 30% higher, at least about 35% higher, at least about 40% higher, at least about 50% higher, than the gel stiffness generated by the mother strain.

Preferably, the mutant generates a viscosity in full fat cow milk added 2% skim milk powder greater than about 105 Pa measured as shear stress in 300 l/s (Pa) after 12 hours of growth in the milk at 37° C. when inoculated in an amount of at least $10^4$ cells per ml of milk in the case of *Lactobacillus delbrueckii* subsp. *bulgaricus* strains and greater than about 75 Pa measured as shear stress in 300 l/s (Pa) after 12 hours of growth in the milk at 37° C. when inoculated in an amount of at least $10^4$ cells per ml of milk in the case of *Streptococcus thermophilus* strains.

In a preferred embodiment, the mutant generates a gel stiffness in full fat cow milk added 2% skim milk powder greater than about 80 Pa after 12 hours of growth in the milk at 37° C. when inoculated in an amount of at least $10^4$ cells per ml of milk in the case of *Lactobacillus delbrueckii* subsp. *bulgaricus* strains and greater than about 140 Pa after 12 hours of growth in the milk at 37° C. when inoculated in an amount of at least $10^4$ cells per ml of milk in the case of *Streptococcus thermophilus* strains.

In a second aspect the present invention is directed to a lactic acid bacteria strain obtainable by the method according to the first aspect of the invention.

In a preferred embodiment the lactic acid bacteria strain is a strain selected from the group consisting of *Lactobacillus delbrueckii* subsp. *bulgaricus* and *Streptococcus thermophilus*. In another preferred embodiment the lactic acid bacteria strain generates a viscosity in full fat cow milk added 2% skim milk powder greater than about 105 Pa measured as shear stress in 300 l/s (Pa) after 12 hours of growth in the milk at 37° C. when inoculated in an amount of $10^1$ cells per ml of milk in the case of *Lactobacillus delbrueckii* subsp. *bulgaricus* strains and greater than about 75 Pa measured as shear stress in 300 l/s (Pa) after 12 hours of growth in the milk at 37° C. when inoculated in an amount of at least $10^4$ cells per ml of milk in the case of *Streptococcus thermophilus* strains.

Preferably, the lactic acid bacteria strain generates a gel stiffness in full fat cow milk added 2% skim milk powder greater than about 80 Pa after 12 hours of growth in the milk at 37° C. when inoculated in an amount of at least $10^4$ cells per ml of milk in the case of *Lactobacillus delbrueckii* subsp. *bulgaricus* strains and greater than about 140 Pa after 12 hours of growth in the milk at 37° C. when inoculated in an amount of at least $10^4$ cells per ml of milk in the case of *Streptococcus thermophilus* strains.

In a third aspect the present invention relates to a lactic acid bacteria strain belonging to the species *Lactobacillus delbrueckii* subsp. *bulgaricus*, selected from the group consisting of: strain CHCC12944, that was deposited with Deutsche Sammlung von Mikroorganimen und Zellkulturen under accession number DSM 24019, strain CHCC12945, that was deposited with Deutsche Sammlung von Mikroorganismen und Zellkulturen under accession number DSM 24020, and mutants and variants of any of these. The mutants and variants show the shear stress and/or gel stiffness characteristics of the deposited strains from which they have been derived.

In a fourth aspect the present invention relates to a lactic acid bacteria strain belonging to the species *Streptococcus thermophilus*, selected from the group consisting of: strain CHCC13235, that was deposited with Deutsche Sammlung von Mikroorganismen und Zellkulturen under accession number DSM 24010, strain CHCC13236, that was deposited with Deutsche Sammlung von Mikroorganismen und Zellkulturen under accession number DSM 24011, and mutants and variants of any of these. The mutants and variants show the shear stress and/or gel stiffness characteristics of the deposited strains from which they have been derived.

In a fifth aspect the present invention relates to a lactic acid bacteria strain belonging to the species *Lactobacillus delbrueckii* subsp. *bulgaricus* resistant to D-cycloserine and/or a functionally equivalent antibiotic having the same or improved gel stiffness and/or shear stress characteristics of strain CHCC12944, that was deposited with the Deutsche Sammlung von Mikroorganismen und Zellkulturen under accession number DSM 24019 or strain CHCC12945, that was deposited with the Deutsche Sammlung von Mikroorganismen und Zellkulturen under accession number DSM 24020.

In a sixth aspect the present invention concerns a lactic add bacteria strain belonging to the species *Streptococcus thermophilus* resistant to D-cycloserine and/or a functionally equivalent antibiotic having the same or improved gel stiffness and/or shear stress characteristics of strain CHCC13235, that was deposited with the Deutsche Sammlung von Mikroorganismen und Zellkulturen under accession number DSM 24010 or strain CHCC13236, that was deposited with the Deutsche Sammlung von Mikroorganismen und Zellkulturen under accession number DSM 24011.

In a seventh aspect the present invention concerns a composition comprising a lactic acid bacteria strain according to the second to sixth aspects of the present invention.

In one embodiment of the present invention the composition comprises, either as a mixture or as a kit-of-parts:
i) a strain belonging to the species *Streptococcus thermophilus* according to the second, fourth or sixth aspect of the invention; and
ii) a strain belonging to the species *Lactobacillus delbrueckii* subsp. *bulgaricus* according to the second, third or fifth aspect of the invention.

The composition in one embodiment preferably comprises at least $10^9$ CFU (cell forming units) of a strain belonging to the species *Lactobacillus delbrueckii* subsp *bulgaricus*; and at least $10^{10}$ CFU of a strain belonging to the species *Streptococcus thermophilus*. The composition in another embodiment comprises at least $10^{11}$ CFU (cell forming units) of a strain belonging to the species *Lactobacillus delbrueckii* subsp *bulgaricus*; and at least $10^{12}$ CFU of a strain belonging to the species *Streptococcus thermophilus*.

The composition in one preferred embodiment may advantageously be usable as a starter culture, and is in frozen, freeze-dried or liquid form.

The present invention in an eighth aspect relates to a method of producing a dairy product, such as a fermented milk product, comprising fermenting a milk substrate with a lactic acid bacteria strain according to any of the second to sixth aspects of the present invention or a composition according to the seventh aspect of the present invention, thereby obtaining a dairy product.

The dairy product produced by this method thereby comprises the lactic acid bacteria strain according to any of the second to sixth aspects of the present invention or the lactic acid bacteria strains of the composition according to the seventh aspect of the present invention, respectively.

In the method, the milk substrate may be fermented with a strain of the invention, such as a strain belonging to the species *Streptococcus thermophilus* before, during, or after the fermentation with a strain of the invention, such as a strain belonging to a *Lactobacillus* species.

Further, the method may include adding an enzyme to the milk substrate before, during and/or after the fermenting, such as an enzyme selected from the group consisting of: an enzyme able to crosslink proteins, transglutaminase, an aspartic protease, chymosin, and rennet.

In a ninth aspect the present invention concerns a dairy product, such as a fermented milk product (e.g. yoghurt or buttermilk) or a cheese (e.g. fresh cheese of pasta filata), obtainable by a method according to the eight aspect of the invention.

The dairy product comprises lactic acid bacteria.

The dairy product may optionally comprise an ingredient selected from the group consisting of: a fruit concentrate, a syrup, a probiotic bacterial culture, a coloring agent, a thickening agent, a flavoring agent, and a preserving agent; and/or which optionally is in the form of a starred type product, a set type product, or a drinkable product.

In a tenth aspect the present invention relates to a dairy product comprising a lactic acid bacteria strain according to any of the second to sixth aspects of the present invention.

In an eleventh aspect the present invention relates to use of a lactic acid bacteria strain according to any of the second to sixth aspects for manufacture of a fermented milk product.

The present invention is further illustrated by the following non-limiting examples.

EXAMPLES

Example 1

Use of D-Cycloserine to Isolate Mutants in *Lactobacillus delbrueckii* Subsp. *Bulgaricus* with Improved Rheological Properties Materials and Methods Strains

*Lactobacillus delbrueckii* subsp. *bulgaricus* CHCC13995
*Lactobacillus delbrueckii* subsp. *bulgaricus* CHCC12944 (D-cycloserine resistant mutant of CHCC13995)
*Lactobacillus delbrueckii* subsp. *bulgaricus* CHCC12945 (D-cycloserine resistant mutant of CHCC13995)

Mutant Isolation

In order to isolate mutants of the *Lactobacillus delbrueckii* subsp. *bulgaricus* strain CHCC13995, cells derived from the growth of a single colony were inoculated into MRS broth containing in the range of 50-100 μg/ml D-cycloserine and grown to saturation. Cells were diluted and plated on MRS plates and colonies were screened in microtiter plates for the ability to grow in the presence of in the range of 50-100 μg/ml D-cycloserine. Typically, 25% of the resulting colonies were identified as fast growers in the presence of D-cycloserine. These were chosen for further study. The selected D-cycloserine resistant mutants were further purified and tested for their ability to grow in milk. During this work it was observed that some of the mutants produced considerably more texture than the parent strain under these conditions.

Rheology

A rheological analysis was done on a StressTech rheometer from Reologica Instruments AB, Sweden, following growth in full fat cow milk with 2% added skim milk powder.

Results

Two mutant derivatives of CHCC13995, designated CHCC12944 and CHCC12945, produced significantly more texture with an Increased shear stress (viscosity) as well as gel stiffness than the mother strain. This was very evident just by stirring a pipette in the fermented milk. Furthermore, it was observed that the amount of whey differed between the various mutants and this became one of the parameters used to select the mutants for further study (see Table 1 below). The mutants selected were those which showed a low level of syneresis: mutant 1 and mutant 11 in the example below (Table 1) corresponds to mutants CHCC12944 and CHCC12945, respectively.

TABLE 1

Mutant 1 and mutant 11 were chosen among the 20 mutants, because of the low volume of whey produced. The empty lanes are mutants that did not coagulate milk. The 2 mutants were designated CHCC12945 and CHCC12944, respectively.

| Mut. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| ml | 4 | 16 | — | 17 | 8 | 8 | 10.5 | 22 | — | 16 | 7 | 5 | 15 | 32 | 11 | — | 16 | 20 | — | — | ml whey after growth for 24 hours in 100 ml B-milk at 43° C.

Figure 2:
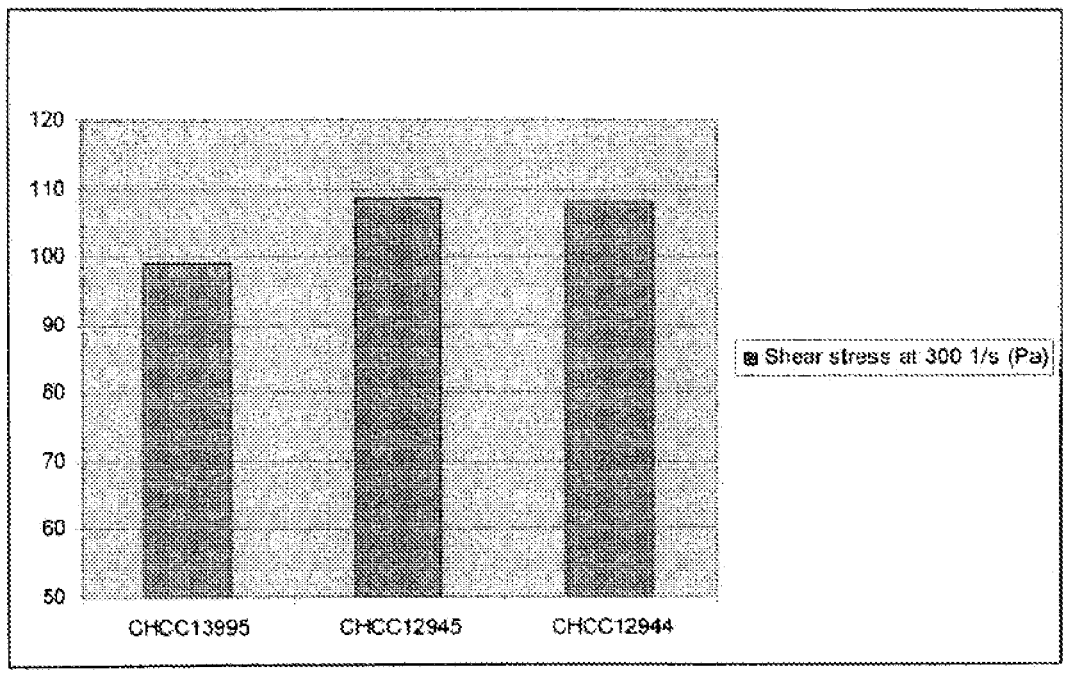
FIG. 2 depicts shear stress (in 300 l/s (Pa)) in full fat milk with 2% skim milk powder at 43° C. for mother strain *Lactobacillus delbrueckii* subsp. *bulgaricus* CHCC13995 and two D-cycloserine mutants of CHCC13995 named CHCC12944 and CHCC12945.
Figure 3:
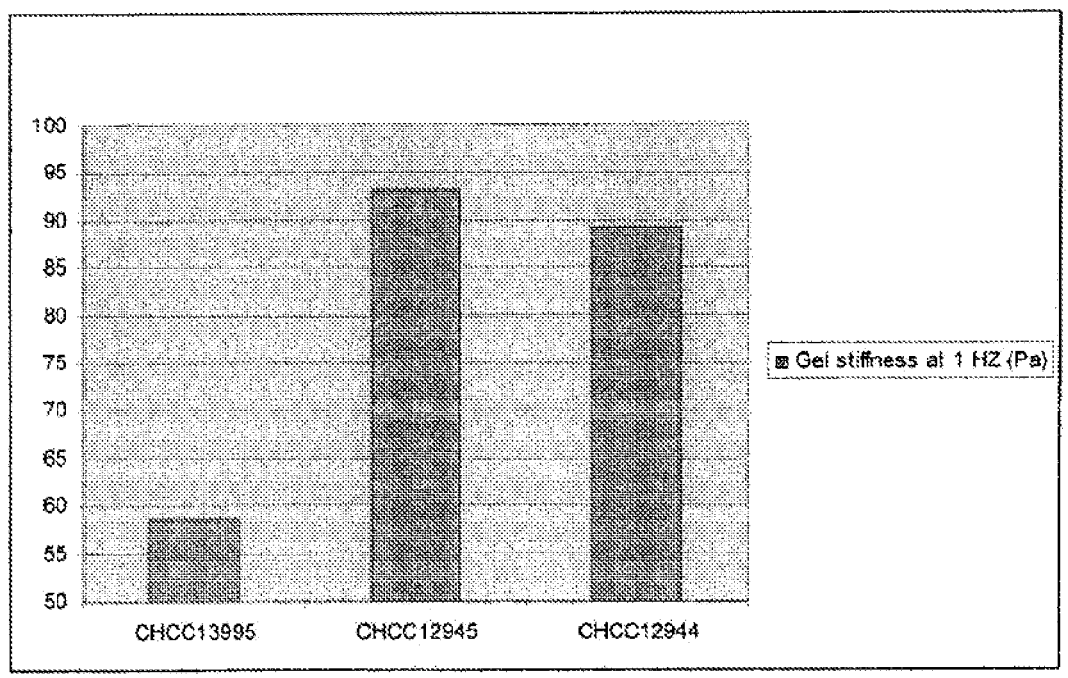
FIG. 3 depicts gel stiffness (in 300 l/s (Pa)) in full fat milk with 2% skim milk powder at 43° C. for mother strain *Lactobacillus delbrueckii* subsp. *bulgaricus* CHCC13995 and two D-cycloserine mutants of CHCC13995 named CHCC12944 and CHCC12945.

The actual rheology tests support the observation of increased thickness (Table 2 and FIGS. 2 and 3). The increase in gel stiffness of the mutants CHCC12945 and CHCC12944 is between 52% and 59%. Shear stress is also higher but not as much as for the gel stiffness (Table 2 and FIGS. 2 and 3).

TABLE 2

| Sample | Shear stress at 300 1/s (Pa) | Gel stiffness at 1 HZ (Pa) |
|---|---|---|
| CHCC13995 | 99 | 58.55 |
| CHCC12945 | 108.5 | 93.20 |
| CHCC12944 | 108 | 89.05 |

One thing is improved rheology but the mutants would be less attractive if other important properties such as acidification were affected. The acidification profile when growing in full fat cow milk with additional 2% skim milk powder at 43° C. is the same for the chosen mutants as for the relevant mother strain (FIG. 1).

Conclusion

The *Lactobacillus delbrueckii* subsp. *bulgaricus* D-cycloserine mutants described herein may be incorporated into a culture, such as a starter culture, which produces a desirable high level of texture.

Example 2

Use of D-Cycloserine to Isolate Mutants in *Streptococcus thermophilus* with Improved Rheological Properties Materials and Methods
Strains
*Streptococcus thermophilus* CHCC13994
*Streptococcus thermophilus* CHCC13236 (D-cycloserine resistant mutant of CHCC13994)
*Streptococcus thermophilus* CHCC13235 (D-cycloserine resistant mutant of CHCC13994)

Mutant Isolation:

In order to isolate mutants of *Streptococcus thermophilus* CHCC13994. cells derived from the growth of a single colony were inoculated into M17+2% lactose broth containing in the range of 50-70 µg/ml D-cycloserine and grown to saturation. Cells were diluted and plated on M17+2% lactose plates and colonies were picked and screened in micro titer plates for the ability to grow in the presence of in the range of 50-70 µg/ml D-cycloserine. Typically, 25% of the resulting colonies were identified as fast growers in the presence of D-cycloserine. These were chosen for further study. The selected D-cycloserine resistant mutants were further purified and tested for their ability to grow in milk. During this work it was observed if some of the mutants produced considerably more texture than the parent strain under these conditions. The amount of whey was also measure as indication of high or low gel stiffness.

Rheology

A rheological analysis was done on a StressTech rheometer from ReoLogica Instruments AB, Sweden, following growth in full fat cow milk with 2% added skim milk powder.

Results

Two mutant derivatives of CHCC13994, designated CHCC13235 and CHCC13236, produced more texture than the mother strain. This was very evident just by stirring a pipette in the fermented milk. Furthermore, it was observed that the amount of whey differed between the various mutants and this became one of the parameters used to select the mutants for further study (see Table 3 below). The mutants selected, no. 9 and no. 13 in table 3, were two showing a low level of syneresis. The 2 mutants were designated CHCC13236 and CHCC13235, respectively.

TABLE 3

2 mutants no. 9 and no. 13 were chosen among the 20 mutants.

| Mut. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| ml | 12 | 20 | 10 | 5.5 | 7 | 10 | 7.5 | 12 | 7 | 22 | 6.5 | — | 6.5 | 7 | 7.5 | 6 | 10 | 10 | 5 | 6 | ml whey after growth for 24 hours in 50 ml B-milk at 37° C.

Figure 4:
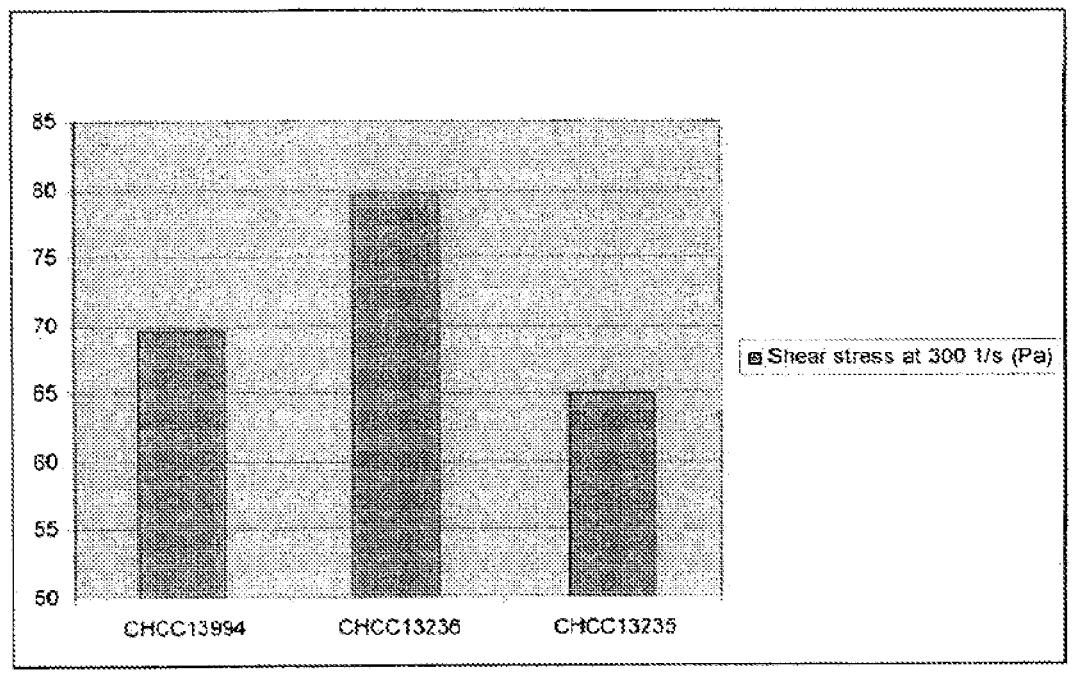
FIG. 4 depicts shear stress (in 300 l/s (Pa)) in full fat milk with 2% skim milk powder at 43° C. for mother strain *Streptococcus thermophilus* CHCC13994 and 2 D-cycloserine mutants of CHCC13994 named CHCC13235 and CHCC13236.
Figure 5:
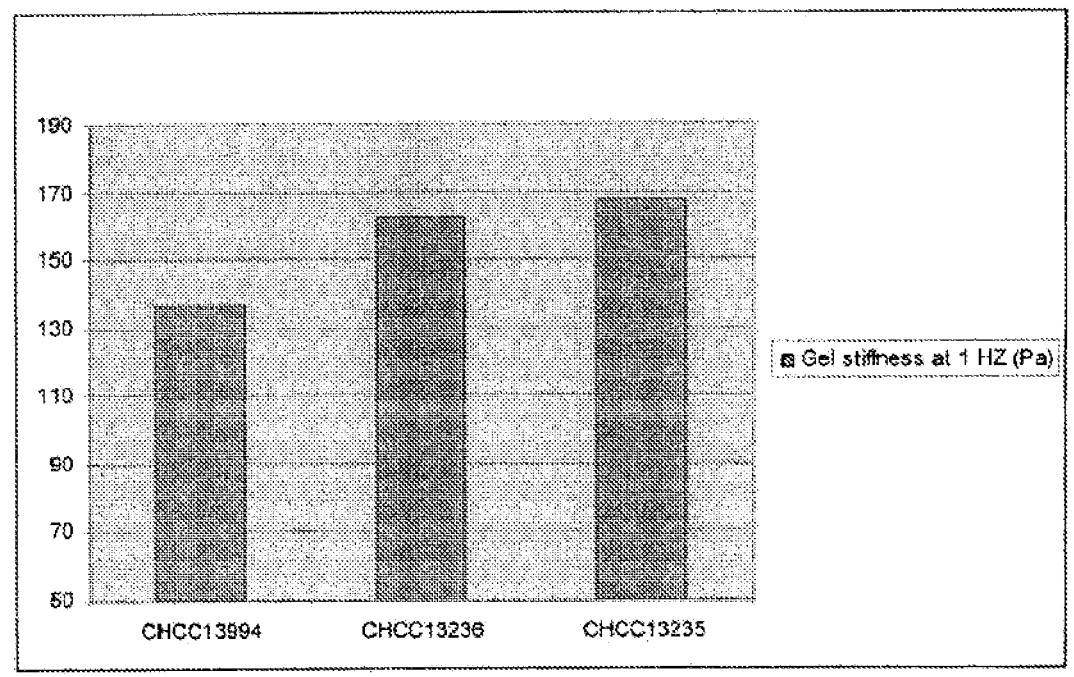
FIG. 5 depicts gel stiffness (in 300 l/s (Pa)) in full fat milk with 2% skim milk powder at 43° C. for mother strain *Streptococcus thermophilus* CHCC13994 and 2 D-cycloserine mutants of CHCC13994 named CHCC13235 and CHCC13236.

The actual rheology tests support the observation of increased thickness (FIG. 4 and FIG. 5). The mutant CHCC13236 had a 15% increase in shear stress and 19% in gel stiffness, where as mutant CHCC13235 only showed an increase in gel stiffness (23%) (Table 4).

TABLE 4

| Sample | Shear stress at 300 1/s (Pa) | Gel stiffness at 1 HZ (Pa) |
|---|---|---|
| CHCC13994 | 69.6 | 136.6 |
| CHCC13236 | 79.7 | 162.5 |
| CHCC13235 | 64.9 | 167.3 |

Regarding acidification, the profile is the same for the chosen mutants as for the relevant another strain (data not shown).

Conclusion

The *Streptococcus thermophilus* D-cycloserine mutants described herein may be incorporated into a culture, such as a starter culture, which produces a desirable high level of texture.

Example 3

Use of *S thermophilus* and *Lb. Delbrueckii* Subsp *Bulgaricus* D-Cycloserine Mutants for Preparation of a Fermented Milk Product Yoghurt was made with a combination of *S. thermophilus* and *Lb. delbrueckii* subsp *bulgaricus*, mixed at a 9:1 ratio and inoculated into full fat cow milk with 2% added skim milk powder. One mixture comprised the parent strains CHCC13994 and CHCC13995; a second comprised *S. thermophilus* D-cycloserine mutant CHCC13236 and *Lb. delbrueckii* subsp *bulgaricus* D-cycloserine mutant CHCC12945 and a third comprised *S. thermophilus* D-cycloserine mutant CHCC13235 and *Lb. delbrueckii* subsp *bulgaricus* D-cycloserine mutant CHCC12945. Comparing the acidification profiles between the three combinations showed that the mixtures with two mutants had a slightly higher final pH than the combination with the parent strains (data not shown). Stirring with a spoon showed that the products made with the D-cycloserine mutants had a noticeably increased resistance to stirring compared to the product with the parent strains. Additionally, the resulting yoghurt was considered to have a more creamy texture and a fresher taste when evaluated by three people.

Deposits and Expert Solution

The strains of *Lactobacillus delbrueckii* subsp. *bulgaricus* CHCC12944, CHCC12945 and CHCC13995 were deposited at DSMZ (Deutsche Sammlung von Mikroorganismen und Zellkulturen GmbH, Inhoffenstr. 7B, D-38124 Braunschweig, Germany) under the accession numbers DSM 24019, DSM 24020, and DSM 24021, respectively, on 22 Sep. 2010.

The strains of *Streptococcus thermophilus* CHCC13235, CHCC13236, and CHCC13994 were deposited at DSMZ (Deutsche Sammlung von Mikroorganismen und Zellkulturen GmbH, Inhoffenstr. 7B, D-38124 Braunschweig, Germany) under the accession numbers DSM 24010, DSM 24011, and DSM 24012, respectively, on 22 Sep. 2010.

The deposits have been made under the conditions of the Budapest Treaty on the International Recognition of the Deposit of Microorganisms for the Purposes of Patent Procedure.

The Applicant requests that a sample of the deposited microorganisms should be made available only to an expert approved by the Applicant.

REFERENCES

Tytgat et al. (2009), Curr. Med. Chem. 16(20): 2566-2580.
Caceres et al. (1997), 3. Bacteriol. 179: 5046-5055.
Holtje (2004), *The Desk Encyclopedia of Microbiology:* 239-258.

All references cited in this patent document are hereby incorporated herein in their entirety by reference.

The invention claimed is:

1. A texturizing lactic acid bacteria strain selected from the group consisting of:
   (a) the D-cycloserine resistant *Lactobacillus delbrueckii* subsp *bulgaricus* strain CHCC12944 deposited with the Deutsche Sammlung von Mikroorganismen and Zellkulturen (DSMZ) under accession number DSM 24019 and mutant strains derived therefrom that are resistant to D-cycloserine and produce the same or more texture as the deposited strain as determined by shear stress and/or gel stiffness when inoculated into fermented milk in the same amount of at least $10^4$ cells/ml as the deposited strain;
   (b) the D-cycloserine resistant *Lactobacillus delbrueckii* subsp *bulgaricus* strain CHCC12945 deposited with the DSMZ under accession number DSM 24020 and mutant strains derived therefrom that are resistant to D-cycloserine and produce the same or more texture as the deposited strain as determined by shear stress and/or gel stiffness when inoculated into fermented milk in the same amount of at least $10^4$ cells/ml as the deposited strain;
   (c) the D-cycloserine resistant *Streptococcus thermophilus* strain CHCC13235 that was deposited with the DSMZ under accession number DSM 24010 and mutant strains derived therefrom that are resistant to D-cycloserine and produce the same or more texture as the deposited strain as determined by shear stress and/or gel stiffness when inoculated into fermented milk in the same amount of at least $10^4$ cells/ml as the deposited strain; and
   (d) the D-cycloserine resistant *Streptococcus thermophilus* strain CHCC13236 deposited with the DSMZ under accession number DSM 24011 and mutant strains derived therefrom that are resistant to D-cycloserine and produce the same or more texture as the deposited strain as determined by shear stress and/or gel stiffness when inoculated into fermented milk in the same amount of at least $10^4$ cells/ml as the deposited strain.

2. The texturizing lactic acid bacteria strain of claim 1, selected from the group consisting of the D-cycloserine resistant *Lactobacillus delbrueckii* subsp *bulgaricus* strain CHCC12944 deposited with the Deutsche Sammlung von Mikroorganismen and Zellkulturen (DSMZ) under accession number DSM 24019 and mutant strains derived therefrom that are resistant to D-cycloserine and produce the same or more texture as the deposited strain as determined by shear stress and/or gel stiffness when inoculated into fermented milk in the same amount of at least $10^4$ cells/ml as the deposited strain.

3. The texturizing lactic acid bacteria strain of claim 1, selected from the group consisting of the D-cycloserine resistant *Lactobacillus delbrueckii* subsp *bulgaricus* strain CHCC12945 deposited with the DSMZ under accession number DSM 24020 and mutant strains derived therefrom that are resistant to D-cycloserine and produce the same or more texture as the deposited strain as determined by shear stress and/or gel stiffness when inoculated into fermented milk in the same amount of at least $10^4$ cells/ml as the deposited strain.

4. The texturizing lactic acid bacteria strain of claim 1, selected from the group consisting of the D-cycloserine resistant *Streptococcus thermophilus* strain CHCC13235 that was deposited with the DSMZ under accession number DSM 24010 and mutant strains derived therefrom that are resistant to D-cycloserine and produce the same or more texture as the deposited strain as determined by shear stress and/or gel stiffness when inoculated into fermented milk in the same amount of at least $10^4$ cells/ml as the deposited strain.

5. The texturizing lactic acid bacteria strain of claim 1, selected from the group consisting of the D-cycloserine resistant *Streptococcus thermophilus* strain CHCC13236 deposited with the DSMZ under accession number DSM 24011 and mutant strains derived therefrom that are resistant to D-cycloserine and produce the same or more texture as the deposited strain as determined by shear stress and/or gel stiffness when inoculated into fermented milk in the same amount of at least $10^4$ cells/ml as the deposited strain.

6. A composition comprising a texturizing lactic acid bacteria strain according to claim 1.

7. The composition according to claim 6, in frozen, freeze-dried or liquid form.

8. The composition according to claim 6 comprising as a mixture or as separate components:
   (i) a *Lactobacillus delbrueckii* subsp *bulgaricus* strain selected from the group consisting of (a) the D-cycloserine resistant strain CHCC12944 deposited with the Deutsche Sammlung von Mikroorganismen and Zellkulturen (DSMZ) under accession number DSM 24019 and mutant strains derived therefrom that are resistant to D-cycloserine and produce the same or more texture as the deposited strain as determined by shear stress and/or gel stiffness when inoculated into fermented milk in the same amount of at least $10^4$ cells/ml as the deposited strain and (b) the D-cycloserine resistant strain CHCC12945 deposited with the DSMZ under accession number DSM 24020 and mutant strains derived therefrom that are resistant to D-cycloserine and produce the same or more texture as the deposited strain as determined by shear stress and/or gel stiffness when inoculated into fermented milk in the same amount of at least $10^4$ cells/ml as the deposited strain; and (ii) a *Streptococcus thermophilus* strain selected from the group consisting of (c) the D-cycloserine resistant CHCC13235 that was deposited with the DSMZ under accession number DSM 24010 and mutant strains derived therefrom that are resistant to D-cycloserine and produce the same or more texture as the deposited strain as determined by shear stress and/or gel stiffness when inoculated into fermented milk in the same amount of at least $10^4$ cells/ml as the deposited strain and (d) the D-cycloserine resistant strain CHCC13236 deposited with the DSMZ under accession number DSM 24011 and mutant strains derived therefrom that are resistant to D-cycloserine and produce the same or more texture as the deposited strain as determined by shear stress and/or gel stiffness when inoculated into fermented milk in the same amount of at least $10^4$ cells/ml as the deposited strain.

9. The composition according to claim 8, in frozen, freeze-dried or liquid form.

10. A method of producing a dairy product, comprising fermenting a milk substrate with a texturizing lactic acid bacteria strain according to claim 1.

11. A method of producing a dairy product, comprising fermenting a milk substrate with a composition according to claim 6.

12. A method of producing a dairy product, comprising fermenting a milk substrate with a composition according to claim 8.

13. A dairy product comprising a texturizing lactic acid bacteria strain according to claim 1.

* * * * *